(12) United States Patent
Laubender et al.

(10) Patent No.: US 9,422,505 B2
(45) Date of Patent: Aug. 23, 2016

(54) CARRIER SYSTEM FOR FRAGRANCES

(71) Applicant: BASF SE, Ludwigshafen (DE)

(72) Inventors: Matthias Laubender, Schifferstadt (DE); Ouidad Benlahmar, Mannheim (DE); Regina Klein, Speyer (DE); Joseph Stracke, Kleinniedesheim (DE); Patrick Leibach, Essingen (DE); Jeremy Ness, Kent (GB)

(73) Assignee: GIVAUDAN S.A., Vernier (CH)

(*) Notice: Subject to any disclaimer, the term of this patent is extended or adjusted under 35 U.S.C. 154(b) by 0 days.

(21) Appl. No.: 14/010,693

(22) Filed: Aug. 27, 2013

(65) Prior Publication Data
US 2014/0065197 A1    Mar. 6, 2014

Related U.S. Application Data

(60) Provisional application No. 61/693,800, filed on Aug. 28, 2012.

(51) Int. Cl.

| | | |
|---|---|---|
| C11B 9/00 | (2006.01) | |
| A61K 8/11 | (2006.01) | |
| A61Q 15/00 | (2006.01) | |
| A61K 8/81 | (2006.01) | |
| A61K 8/04 | (2006.01) | |
| C11D 3/00 | (2006.01) | |
| C11D 3/50 | (2006.01) | |
| A61Q 5/02 | (2006.01) | |
| A61Q 5/12 | (2006.01) | |

(52) U.S. Cl.
CPC . *C11B 9/00* (2013.01); *A61K 8/044* (2013.01); *A61K 8/11* (2013.01); *A61K 8/8129* (2013.01); *A61K 8/8152* (2013.01); *A61Q 15/00* (2013.01); *C11D 3/0015* (2013.01); *C11D 3/505* (2013.01); *A61K 2800/412* (2013.01); *A61K 2800/594* (2013.01); *A61Q 5/02* (2013.01); *A61Q 5/12* (2013.01)

(58) Field of Classification Search
None
See application file for complete search history.

(56) References Cited

U.S. PATENT DOCUMENTS

| 5,292,835 A | 3/1994 | Jahns et al. |
|---|---|---|
| 5,576,282 A | 11/1996 | Miracle et al. |
| 6,306,812 B1 | 10/2001 | Perkins et al. |
| 6,326,348 B1 | 12/2001 | Vinson et al. |
| 2003/0125222 A1 | 7/2003 | Jahns et al. |
| 2010/0068525 A1 | 3/2010 | Jung et al. |
| 2010/0286018 A1 | 11/2010 | Hentze et al. |
| 2012/0058929 A1 | 3/2012 | Laubender et al. |
| 2012/0076843 A1 | 3/2012 | Jung et al. |

FOREIGN PATENT DOCUMENTS

| EP | 0457154 A1 | 11/1991 |
|---|---|---|
| WO | WO-99/05242 A1 | 2/1999 |
| WO | WO-01/49817 A2 | 7/2001 |
| WO | WO-2005/105291 A1 | 11/2005 |
| WO | WO-2008/061885 A2 | 2/2008 |
| WO | WO-2008/058868 A1 | 5/2008 |
| WO | WO-2008071649 A2 | 6/2008 |
| WO | WO-2009/090169 A1 | 7/2009 |
| WO | WO-2010119020 A1 | 10/2010 |
| WO | WO-2010/145993 A2 | 12/2010 |
| WO | WO-2014/032920 A1 | 3/2014 |

OTHER PUBLICATIONS

Suspension polymerization [http://en.wikipedia.org/wiki/Suspension_polymerization, last visit on Mar. 21, 2015].*
Arian vab Asten, "The importance of GC and GC-MS in perfume analysis", Trends in analytical chemistry, vol. 21, Nos. 9+10, pp. 698-708, 2002.*
International Search Report for PCT/EP2013/066480, mailing date Nov. 7, 2013.

* cited by examiner

*Primary Examiner* — Ernst V Arnold
*Assistant Examiner* — Kyung Sook Chang
(74) *Attorney, Agent, or Firm* — Norris McLaughlin & Marcus PA

(57) ABSTRACT

The present invention relates to a carrier system for fragrances, to the production thereof and to the use of the carrier system in laundry and cosmetic formulations.
Accordingly, the present invention is directed to a microcapsule comprising a core of hydrophobic material composed of at least one fragrance or perfume and a microcapsule shell obtainable by the suspension polymerization of the following monomers:
- (a) one or more $C_1$-$C_{24}$-alkyl ester(s) of (meth)acrylic acid (monomer A),
- (b) one or more bi- or polyfunctional monomers (monomer B) and
- (c) optionally, one or more other ethylenically unsaturated monomers (monomer C), wherein the shear rate for the preparation of the emulsion lies in the range of from 150 to 500 rpm and the stirring time for the preparation of the emulsion lies in the range of from 15 min to 180 min.

17 Claims, No Drawings

CARRIER SYSTEM FOR FRAGRANCES

RELATED APPLICATIONS

This application claims benefit (under 35 USC 119(e)) of U.S. Provisional Application Ser. No. 61/693,800, filed Aug. 28, 2012, which is incorporated herein by reference in its entirety.

The present invention relates to a carrier system for fragrances, to the production thereof and to the use of the carrier system in laundry and cosmetic formulations.

Most washing and cleaning as well as cosmetic formulations contain fragrances or perfumes in order to confer a pleasant smell to the formulation itself or to the surface, be it textile, skin or hair, onto which the formulation is applied. The fragrances or perfumes are often compounds having two or more conjugated double bonds and which are sensitive to various chemicals and to oxidation. Consequently, unwanted interactions with other ingredients of the formulations such as surfactants may lead to an alteration of the fragrance note. In addition, fragrances or perfumes are mostly highly volatile. As a result a large part of the quantity of fragrance originally added to the formulations has volatilized before the time of application and the remaining quantity of fragrance actually applied onto the treated surface also volatilizes within a short time. To overcome these problems it has already been proposed to incorporate the fragrances or perfumes in microcapsules into the formulations. These microcapsules enable the valuable fragrance or perfume to be distributed relatively homogeneously in a formulation, without having to expose it to the other constituents during storage. Suitable selection of the shell of the capsule also allows effects to be achieved in this way such as retarded release or release on demand upon rubbing.

For example, WO 01/49817 discloses microcapsules, for the encapsulation of hydrophobic material, having a shell obtainable by the polymerization of from 30 to 100% by weight of one or more $C_1$-$C_{24}$-alkyl ester(s) of acrylic acid and/or methacrylic acid, from 0 to 70% by weight of a bi- or polyfunctional monomer, and from 0 to 40% by weight of other monomers. These micro-capsules are reported to have an average diameter of 1 to 100 µm and to find their applications either in detergent compositions for textiles or in cleaning product compositions for non textile surfaces such as skin or hair.

WO 2010/119020 writes on microcapsules, for the encapsulation of hydrophobic material, having a shell obtainable by the polymerization of from one or more $C_1$-$C_{24}$-alkyl ester(s) of acrylic acid and/or methacrylic acid and methacrylic acid, the methacrylic acid being present in the shell in an amount of 20 to 60% by weight, and/or 1,4-butanediol diacrylate in an amount of 10 to 50% by weight and/or pentaerythrityl triacrylate in an amount of 10 to 50% by weight and/or ethylene glycol dimethacrylate in an amount of 10 to 50% by weight.

EP 0457 154 discloses microcapsule with a shell of polymer composed of 30 to 100% by weight of $C_1$-$C_{24}$-alkyl ester(s) of acrylic acid and/or methacrylic acid, 0 to 80% by weight of a bi- or polyfunctional monomer and 0 to 40% by weight of other monomers, for the encapsulation of colour formers used in pressure-sensitive recording material.

WO 2008/071649 discloses microcapsule with a shell of polymer composed of 30 to 90% by weight of $C_1$-$C_{24}$-alkyl ester(s) of acrylic acid and/or methacrylic acid, 10 to 70% by weight of a bi- or polyfunctional monomer and 0 to 30% by weight of other monomers, for the encapsulation of hydrophobic material for us in textile, building materials and heat transfer fluid.

In order to preserve the volatile fragrances or perfumes in microcapsules for applications in laundry and cosmetic formulations, the microcapsules must enclose the volatile substance particularly efficiently. It was therefore an object of the present invention to provide a microcapsule with improved imperviousness for volatile substances and a process for the production thereof. Another object of the invention was to ensure a slow release or a release on demand of the fragrances or perfumes after application onto the treated surface.

This object is surprisingly achieved by the microcapsules according to claims 1 to 10, the use thereof according to claims 11 to 14 and the process for manufacturing the microcapsules according to claims 15 to 17.

Accordingly, the present invention is directed to a microcapsule comprising a core of hydrophobic material composed of at least one fragrance or perfume and a microcapsule shell obtainable by the suspension polymerization of the following monomers:
(a) one or more $C_1$-$C_{24}$-alkyl ester(s) of (meth)acrylic acid (monomer A),
(b) one or more bi- or polyfunctional monomers (monomer B) and
(c) optionally, one or more other ethylenically unsaturated monomers (monomer C),
wherein the shear rate for the preparation of the emulsion lies in the range of from 150 to 500 rpm and the stirring time for the preparation of the emulsion lies in the range of from 15 min to 180 min.

With regard to the shear rate, the preparation of the emulsion is preferably achieved at a shear rate of from 130 to 400 rpm, more preferably of from 150 to 350 rpm.

With regard to the stirring time, the emulsion premix of the suspension polymerization is preferably achieved at a stirring time of from 20 min to 90 min, more preferably from 20 min to 40 min. In a preferred embodiment, the microcapsule according to the invention has a mean diameter of from 10 µm to 60 µm, preferably from 25 µm to 50 µm, even more preferably from 30 µm to 45 µm.

With regard to the amounts, in which monomers A, B and C are present in the microcapsule shell, there are preferred ranges. Thus a microcapsule according to the invention, which consists essentially of the following monomers in copolymerized form:
(a) from 20 to 60% by weight of monomer A,
(b) from 20 to 60% by weight of monomer B,
(c) from 0 to 60% by weight of monomer C,
forms a preferred embodiment of the present invention.

Another preferred embodiment is a microcapsule according to the invention, which consists essentially of the following monomers in copolymerized form:
(a) from 25 to 45% by weight of monomer A,
(b) from 25 to 45% by weight of monomer B,
(c) from 30 to 50% by weight of monomer C, Monomer A is a linear or branched $C_1$-$C_{24}$-alkyl ester(s) of acrylic acid and/or methacrylic acid, preferably a $C_1$-$C_4$-alkyl ester(s) of acrylic acid and/or methacrylic. Suitable monomers A include methyl acrylate, methyl methacrylate, ethyl acrylate, ethyl methacrylate, n-propyl acrylate, n-propyl methacrylate, isopropyl acrylate, isopropyl methacrylate, n-butyl acrylate, isobutyl acrylate, tert-butyl acrylate, n-butyl methacrylate, isobutyl methacrylate, tert-butyl methacrylate, cyclohexyl acrylate, cyclohexyl methacrylate, octyl acrylate, octyl methacrylate, 2-ethylhexyl acrylate, 2-ethylhexyl methacrylate, dodecyl acrylate, lauryl acrylate, cetyl acrylate, octadecyl acrylate, isodecyl acrylate. $C_1$-$C_{24}$-alkyl ester(s) of acrylic acid and/or methacrylic acid are generally understood to mean not just the pure alkyl esters, but also modified compounds, such as alkylamides of acrylic acid or vinyl alkyl ethers. Nonexclusive examples are: tert-butylacrylamide, N,N-dimethylaminoethylmethacrylat, N,N-diethylaminoethylmethacrylat and acrylamide. Monomer A is preferably methyl methacrylate.

Monomer B is 1,4-butanediol diacrylate (BDA2) and/or hexanediol diacrylate (HDDA) and/or pentaerythrityl triacrylate and/or pentaerythrityl tetraacrylate (PETIA—mixture of pentaerythrityl triacrylate and pentaerythrityl tetraacrylate) and/or ethylene glycol dimethacrylate (EDGMA) and/or trimethylolpropane tricacrylate (TMPTA).

Monomer B is preferably a mixture of pentaerythrityl triacrylate and pentaerythrityl tetraacrylate (PETIA) or 1,4-butanediol diacrylate (BDA2).

Monomer C is an ethylenically unsaturated monomer. Suitable monomers C include methacrylic acid, acrylic acid, 2-acrylamido-2-methyl propanesulfonic acid, 2-hydroxyethyl acrylate, 2-hydroxypropyl acrylate, 4-hydroxybutyl acrylate, diethylene glycol monoacrylate, 4-hydroxybutyl vinyl ether, N,N-methylenebisacrylamide, ethyldiglycole acrylate, methyl ethylene glycol methacrylate, methyl diethylene glycole methacrylate, 2-hydroxyethyl methacrylate, hydroxypropyl methacrylate, hydroxyethyl imidazole methacrylate, glycidyl methacrylate, ureido methacrylate, 1,4-cyclohexane dimethanol monovinyl ether, sodium allylsulfonate. Monomer C is preferably methacrylic acid A fragrance is understood to mean all organic substances which have a desired olfactory property. They include all fragrances used customarily in perfumery. They may be compounds of natura, semi-synthetic or synthetic origin. Preferred fragrances can be assigned to the substance classes of the hydrocarbons, aldehydes or esters. The fragrances also include natural extracts and/or essences which may comprise complex mixtures of constituents, such as orange oil, lemon oil, rose extract, lavender, musk, patchouli, balsam essence, sandalwood oil, pine oil and cedar oil.

The fragrances can be used as pure substances or in a mixture with one another. The fragrance can form the core of the microcapsules as the sole hydrophobic material. Alternatively, the microcapsules may comprise a further hydrophobic material in addition to the fragrance, in which the fragrance is dissolved or dispersed. For example, in the case of use of fragrances which are solid at room temperature, the use of a hydrophobic material which is liquid at room temperature as solution or dispersant is advantageous.

It is equally possible to increase the hydrophobicity of a fragrance by adding a further hydrophobic material to this fragrance or odorant.

Preferably, the fragrance or the mixture of fragrances makes up 1 to 100% by weight, preferably 20 to 100% by weight, even more preferably 40 to 99% by weight of the hydrophobic core mate-rial. The hydrophobic material is liquid at temperatures below 100° C., preferably at temperatures below 60° C. and more preferably at room temperature.

The microcapsules according to the invention are obtainable by polymerizing in an emulsion the monomer or monomer mixture which forms the shell in the oil phase of a stable oil-in-water emulsion, where the oil phase consists of a hydrophobic material and at least one fragrance or perfume. The process is thus defined as suspension polymerization. Before the start of the polymerization, the monomer or monomer mixture can be dissolved in the oil phase, which forms the disperse phase of the oil-in-water emulsion. It is however also possible to disperse the solvent and add the monomers and the free radical initiator to the dispersion. A further possibility is to place the solvent and monomers in dispersion and to add just the free radical initiator subsequently. Since the hydrophobic material should be very substantially microencapsulated in the emulsion, it is possible with preference to use only those hydrophobic materials whose solubility in water is limited. The solubility should preferably not exceed 5% by weight.

As a general procedure, a mixture of water, protective colloid and/or ionic emulsifiers and the above-described oil phase is dispersed at a low shear rate with an anchor-type stirring blade or with a MIG-stirrer in order to yield a stable oil-in-water emulsion having the desired oil drop size. The shear rate lies in the range from 150 rpm to 500 rpm (revolutions per minute), preferably from 200 rpm to 400 rpm, more preferably from 200 rpm to 350 rpm.

The hydrophobic materials which can be used for the oil phase include all kinds of oils, such as vegetable oils, animal oils, mineral oils, paraffins, chloroparaffins, fluorohydrocarbons and other synthetic oils. Typical and non-limiting examples are sunflower oil, rapeseed oil, olive oil, peanut oil, soybean oil, kerosene, benzene, toluene, butane, pentane, hexane, cyclohexane, chloroform, carbon tetrachloride, chlorinated diphenyls and silicone oil. It is also possible to use hydrophobic materials with a high boiling point, e.g. diethyl phthalate, dibutyl phthalate, diisohexyl phthalate, dioctyl phthalate, alkylnaphthalene, dodecylbenzene, terphenyl, partly hydrogenated terphenyls, Ethylhexyl Palmitate, Capric/Caprylic-Triglyceride, PPG-2 Myristyl Ether Propionate; PPG-5 Ceteth-20; $C_{12-15}$ Alkyl Benzoate, Mineral Oil (CAS: 8042-47-5); Cetearyl Ethylhexanoate; Dimethicone; Polyisobutylene.

The optional hydrophobic material comprising the fragrance or odorant or consisting thereof is selected such that it can be emulsified in water at temperatures between its melting point and the boiling point of water. Low viscosity hydrophobic materials have a Brookfield viscosity of <5 Pa*s (measured at 23° C. with spindle 5 at 20 rev./s to DIN EBN ISO 3219).

The core of the microcapsules is formed by the hydrophobic material emulsified in water. The hydrophobic material serves simultaneously as a solvent or dispersant for the monomer mixture used in the preparation of the capsule shell by polymerization. The polymerization then takes place in the oil phase of the stable oil-in-water emulsion which preparation is described above. While the monomers are essentially soluble in the oil, they form, in the course of polymerization, in the individual oil droplets, oligo- and polymers which are soluble neither in the oil phase nor in the water phase of the oil-in-water emulsion and migrate to the interface between the oil droplets and the water phase. In the course of further polymerization, they form the wall material which finally encloses the hydrophobic material as the core of the microcapsules.

To form a stable oil-in-water emulsion, protective colloids and/or emulsifiers are generally used. Suitable protective colloids are, for example, cellulose derivatives such as hydroxyethylcellulose, carboxymethylcellulose and methylcellulose, polyvinylpyrrolidone and copolymers of N-vinylpyrrolidone, polyvinyl alcohols and partially hydrolyzed polyvinyl acetates. Particular preference is given to the polyvinyl alcohols. In addition, it is also possible to use gelatin, gum arabic, xanthan gum, alginates, pectins, degraded starches and casein. Ionic protective colloids may also find use. The ionic protective colloids used may be polyacrylic acid, polymethacrylic acid, copolymers of acrylic acid and methacrylic acid, sulfo-containing water-soluble polymers with a content of sulfoethyl acrylate, sulfoethyl methacrylate or sulfopropyl methacrylate, and polymers of N-(sulfoethyl)maleimide, 2-acrylamido-2-alkylsulfonic acids, styrenesulfonic acids and formaldehyde, and also condensates of phenolsulfonic acids and formaldehyde. The protective colloids are generally added in amounts of 0.1 to 10% by mass, based on the water phase of the emulsion. The polymers used as ionic protective colloids preferably have mean molar masses $M_w$ of 500 to 1 000 000 g/mol, preferably 1000 to 500 000 g/mol.

The polymerization is generally effected in the presence of polymerization initiators which form free radicals. For this purpose, it is possible to use all customary peroxo and azo compounds in the amounts customarily used, for example from 0.1 to 5% by mass, based on the mass of the monomers to be polymerized. Preference is given to those polymerization initiators which are soluble in the oil phase or in the monomers. Examples thereof are t-butyl peroxyneodecanoate, t-butyl peroxypivalate, t-amyl peroxypivalate, dilauroyl peroxide, t-amyl peroxy-2-ethylhexanoate and the like.

The polymerization of the oil-in-water emulsion is performed typically at 20 to 100° C., preferably at 40 to 90° C. Typically, the polymerization is undertaken at standard pressure, but can also be effected at elevated or reduced pressure, for example in the range from 0.5 to 20 bar. The rate of polymerization can be controlled in a known manner through the selection of the temperature and of the amount of polymerization initiator. On attainment of the polymerization temperature, the polymerization is appropriately continued for a further period, for example 2 to 6 hours, in order to complete the conversion of the monomers.

Particular preference is given to a mode of operation in which, during the polymerization, the temperature of the polymerizing reaction mixture is varied continuously or periodically, for example increased continuously or periodically. This is done, for example, with the aid of a program with rising temperature.

For this purpose, the total polymerization time can be divided into two or more periods. The first polymerization period is characterized by a slow decomposition of the polymerization initiator. In the second polymerization period and any further polymerization periods, the temperature of the reaction mixture is increased, in order to accelerate the decomposition of the polymerization initiators. The temperature can be increased in one step or in two or more steps, or continuously in a linear or nonlinear manner. The temperature difference between the start and the end of the polymerization may be up to 60° C. In general, this difference is 3 to 40° C., preferably 3 to 30° C.

The microcapsule dispersions obtained by one of the procedures outlined above can subsequently be spray dried in a customary manner. To facilitate the redispersion of the spray dried microcapsules, additional amounts of emulsifier and/or protective colloid can optionally be added to the dispersions before the spray drying. Suitable emulsifiers and protective colloids are those specified above in connection with the production of the microcapsule dispersions. In general, the aqueous microcapsule dispersion is atomized in a hot air stream which is conducted in co-current or counter-current, preferably in co-current, with the spray mist. The inlet temperature of the hot air stream is typically in the range from 100 to 200° C., preferably 120 to 160° C., and the outlet temperature of the air stream is generally in the range from 30 to 90° C., preferably 60 to 80° C. The aqueous microcapsule dispersion can be sprayed, for example, by means of one-substance or multisubstance nozzles, or by means of a rotating disk. The spray dried microcapsules are normally deposited using cyclones or filter separators.

The microcapsules thus obtainable preferably have a mean diameter in the range from 25 to 50 μm, more preferably from 25 to 45 μm and most preferably from 30 to 45 μm. The inventive microcapsules have the advantage of protecting volatile substances from evaporation efficiently.

Fabric and Home Care Formulation

The present invention further provides a fabric and home care composition comprising microcapsules as described above. In one embodiment, the fabric and home care composition of the present invention is a liquid or solid laundry detergent composition. In another embodiment, the fabric and home care composition of the present invention is a liquid fabric softener and conditioner. In a further embodiment, the fabric and home care composition of the present invention is a hard surface cleaning composition, preferably wherein the hard surface cleaning composition impregnates a nonwoven substrate. As used herein "impregnate" means that the hard surface cleaning composition is placed in contact with a nonwoven substrate such that at least a portion of the nonwoven substrate is penetrated by the hard surface cleaning composition, preferably the hard surface cleaning composition saturates the nonwoven substrate.

In another embodiment the fabric and home care composition is a dish cleaning composition, such as liquid hand dishwashing compositions, solid automatic dishwashing compositions, liquid automatic dishwashing compositions, and tab/unit does forms of automatic dishwashing compositions.

Quite typically, fabric and home care compositions herein such as laundry detergents, laundry detergent additives, hard surface cleaners, synthetic and soap-based laundry bars, fabric softeners and fabric treatment liquids, solids and treatment articles of all kinds will require several adjuncts, though certain simply formulated products, such as bleach additives, may require only, for example, an oxygen bleaching agent and a surfactant as described herein. A comprehensive list of suitable laundry or cleaning adjunct materials can be found in WO 99/05242.

Common cleaning adjuncts include builders, enzymes, polymers not discussed above, bleaches, bleach activators, catalytic materials and the like excluding any materials already defined hereinabove. Other cleaning adjuncts herein can include suds boosters, suds suppressors (antifoams) and the like, diverse active ingredients or specialized materials such as dispersant polymers (e.g., from BASF Corp. or Rohm & Haas) other than those described above, color speckles, silvercare, anti-tarnish and/or anti-corrosion agents, dyes, fillers, germicides, alkalinity sources, hydrotropes, anti-oxidants, enzyme stabilizing agents, pro-perfumes, perfumes, solubilizing agents, carriers, processing aids, pigments, and, for liquid formulations, solvents, chelating agents, dye transfer inhibiting agents, dispersants, brighteners, suds suppressors, dyes, structure elasticizing agents, fabric softeners, anti-abrasion agents, hydrotropes, processing aids, and other fabric care agents, surface and skin care agents. Suitable examples of such other cleaning adjuncts and levels of use are found in U.S. Pat. Nos. 5,576,282, 6,306,812 B1 and 6,326,348 B1.

The composition solution pH is chosen to be the most complimentary to a target surface to be cleaned spanning broad range of pH, from about 5 to about 11. The compositions are preferably employed at concentrations of from about 200 ppm to about 10,000 ppm in solution. The water temperatures preferably range from about 5° C. to about 100° C.

For use in laundry cleaning compositions, the compositions are preferably employed at concentrations from about 200 ppm to about 10000 ppm in solution (or wash liquor). The water temperatures preferably range from about 5° C. to about 60° C. The water to fabric ratio is preferably from about 1:1 to about 20:1.

Cosmetic Formulation

The present invention further provides a cosmetic formulation comprising microcapsules as described above. For instance, the liquid microcapsule formulations or microcapsule powders can be used especially for skin- or hair-care formulations. The microcapsules according to the invention are specifically suitable in surfactant-containing formulations.

The cosmetic formulations comprise the microcapsules according to the invention preferably in an amount of from about 0.01 to 20% by weight, particularly preferably 0.05 to 10% by weight, in particular 0.1 to 5% by weight, based on the total weight of the composition.

In a preferred embodiment, the cosmetic formulation is a hair care formulation, i.e. a shampoo or a hair conditioner.

In another preferred embodiment, the cosmetic formulation is a skin care formulation.

In general for the cosmetic formulation according to the invention, the pH is adapted to its use in conjunction with the body. Preferably, the pH of the cosmetic formulation according to the invention is at least 3, more preferably at least 4. For example the pH may be at least 5, more preferably at least 5.5. Preferably, the pH is no more than 10, more preferably no more than 9 and most preferably no more than 8. The pH of the cosmetic formulation may also be adapted to that of the body and be no more than 7.

The cosmetic formulation of the present invention preferably contains at least one surfactant, preferably from 1% to 40% by weight of the total weight of the formulation. More preferably, the cosmetic formulation of the present invention contains at least 5 wt % of at least one surfactant. Preferably, the cosmetic formulation of the present invention contains no more than 20 wt % of at least one surfactant, more preferably no more than 15 wt %.

The one or more surfactants may selected from the groups of anionic surfactants such as alkyl sulfates, alkyl ether sulfates, alkylsulfonates, alkylarylsulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactant(s) are, for example, alkylbetaines, alkylamidopropylbetaines, alkylsulfobetaines, alkyl glycinates, alkyl carboxyglycinates, alkyl amphoacetates or -propionates, alkyl amphodiacetates or -dipropionates.

For example, cocodimethylsulfopropylbetaine, laurylbetaine, cocamidopropylbetaine or sodium cocamphopropionate can be used.

Suitable nonionic surfactant(s) are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 moles per mole of alcohol. In addition, alkylamine oxides, mono- or dialkylalkanolamides, fatty acid esters of polyethylene glycols, ethoxylated fatty acid amides, alkyl polyglycosides or sorbitan ether esters are suitable.

Furthermore, the hair care formulation can comprise cationic surfactants, such as quaternary ammonium compounds, for example cetyltrimethylammonium chloride, behentrimethylammonium methosulfate.

In addition, the hair care formulation according to the invention can comprise one or more rheology modifiers, such as, for example, sodium chloride, PEG-55, propylene glycol oleate, PEG-120 methylglucose dioleate and others, and also one or more preservatives, further active ingredients and auxiliaries and water.

In the hair care formulation according to the invention, in order to achieve certain effects, optionally one or more further ingredients such as conditioning polymers can be used. These conditioning polymers include, for example, the cationic polymers with the INCI name Polyquaternium, in particular copolymers of vinylpyrrolidone/N-vinylimidazolium salts, copolymers of N-vinylpyrrolidone/dimethylaminoethyl methacrylate, quaternized with diethyl sulfate, copolymers of N-vinylcaprolactam/N-vinylpyrrolidone/N-vinylimidazolium salts; cationic cellulose derivatives (Polyquaternium-4 and -10), acrylamide copolymers (Polyquaternium-7). It is also possible to use protein hydrolysates, and conditioning substances based on silicone compounds, for example polyalkylsiloxanes, polyarylsiloxanes, polyarylalkylsiloxanes, polyethersiloxanes or silicone resins. Further suitable silicone compounds are dimethicone copolyols (CTFA) and aminofunctional silicone compounds, such as amodimethicone (CTFA). In addition, cationic guar derivatives such as guar hydroxypropyltrimonium chloride (INCI) can be used.

Further suitable cosmetically acceptable ingredients contained in the heir care formulation according to the invention can also be nonionic polymers, siloxane-containing, water-soluble or water-dispersible polymers, e.g. polyether siloxanes.

Further suitable components are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are commercially available, for example, under the name cyclomethicone.

A particular hair care composition in which the copolymer according to the invention is used is a hair conditioner. A second particular aqueous composition in which the polymer of this invention is useful is a shampoo, and especially a conditioning shampoo. Typical components of a hair conditioner or a conditioning shampoo, in addition to the copolymer and surfactant mentioned previously, include sufficient base or acid to attain a pH of 4 to 6.75, preferably 4.5 to 6.75, and more preferably 5 to 6.5; and optional ingredients, including silicones, pearlizing agents, vitamins, oils, fragrances, dyes, biocides.

EXAMPLES

The invention is described further hereinafter by examples:
Figures in % are percentages by weight, unless explicitly stated otherwise.

All microcapsules displayed in table 1 were prepared according to the following procedure:
I) Microcapsule Synthesis For the production of the microcapsules, the following substances were used:

Oil 1: mineral oil hydrogenated under high pressure, with a viscosity of approx. 68 mm²/s at 40° C. and a solidification point of −21° C. (white oil).
Oil 2: Caprylic/Capric Triglyceride (JCIC: Caprylic/Capric Acid Triglyceride)
Odorant A : Dial M©
Protective colloids:
Protective colloid 1: methylhydroxypropylcellulose (with a Brookfield viscosity (at 20° C., 20 rpm, 2%) of 90-125 mPas), 5% by weight solution in water.
Protective colloid 2: polyvinyl alcohol solution: 10% by weight in water, degree of hydrolysis 79%, mean degree of polymerization PW: 1900
Monomer abbreviations:
MMA methyl methacrylate
MAA methacrylic acid
BDA2 1,4-butanediol diacrylate
PETIA pentaerythrityl tri-tetraacrylate Example 1

| Water phase: | |
|---|---|
| 257.06 g | water |
| 81.87 g | protective colloid 1 |
| 20.47 g | protective colloid 2 |
| 0.91 g | of a 2.5% by weight aqueous sodium nitrite solution |

| Oil phase: | |
|---|---|
| 153.83 g | odorant A |
| 35.91 g | oil |
| 14.28 g | MMA |
| 19.04 g | PETIA |
| 14.28 g | MAA |

| Feed 1: | |
|---|---|
| 0.95 g | tert-butyl peroxyneodecanoate |

| Feed 2: | |
|---|---|
| 6.97 g | of a 10% by weight aqueous tert-butyl hydroperoxide solution |

| Feed 3: | |
|---|---|
| 9.76 g | of a 10% aqueous ascorbic acid solution |

The water phase was initially charged at room temperature. The oil phase and feed 1 were pre-mixed. Addition of the mixture of the oil phase and of feed 1 was followed by dispersion with an anchor-type stirring blade at 250 rpm for 40 minutes. The emulsion formed was heated to 70° C. within 60 minutes, and to 85° C. within a further 60 minutes, and kept at 85° C. for two hours. Feed 1 was added to the microcapsule dispersion formed. Feed 2 was metered in within 50 minutes, in the course of which the mixture was cooled to room temperature. The microcapsule dispersion formed possessed a solid content of 40.4% and a particle size of 37.4 μm (measured by Fraunhofer diffraction, determined per volume average).

II) Tests in Laundry Formulation—
Fragrance leakage test:
Fabric Softener samples containing 0.5wt % encapsulated fragrance equivalent were submitted to 2 months storage at a temperature of 37° C. in sealed glass bottles. 1 g Isolute bulk sorbent Type HM-N (ex Separtis GmbH, Switzerland) was mixed with 10 ml n-Pentane and 2 g of Fabric Softenerbase. The mixture was stirred during 30 minutes on a magnetic stirrer at maximum speed. After phase separation was completed, the organic phase was transferred into an Eppendorf tube and stored for 15 minutes in a freezer (−18° C.). The cold Eppendorf tube was then centrifuged in an Eppendorf centrifuge at maximum speed for 15 seconds. The clear pentane phase was transferred into GC vial and analysed by split-splitless capillary gas chromatography, without further purification. Fragrance leakage results are shown in Table 1.

Analysis of the release behavior:
The Fabric Softener examples above were also tested for their olfactory performance on dry cloth. A 35 g sample of each Softener was used to wash a standard load of washing in a Miele Front Loading Automatic washing machine on the 40° C. quick wash setting, with a 900 rpm spin speed. The standard load consisted of 2.5 kg laundry, inclusive of a number of terry towelling test cloths (white face cloths, 25×25 cm). The test flannels were then dried by both tumble drying (Miele tumble driers set to "cupboard dry") and indoor line drying under controlled conditions.

Twenty-four hours after washing, the performance of the test cloths was evaluated by a panel of eight expert assessors, experienced and trained in such assessments. Each assessor scores the cloths on an individual basis and then the results are collated, averaged and analysed for statistical significance. In all cases the cloths are evaluated as received ("non-rubbed") and after a controlled rubbing ("rubbed") to break some of the capsules.

A standard 0-10 scoring system is used, where:
0—No odour
2—Odour is barely perceivable
4—Weak fragrance but perceivable
6—Easily perceivable
8—Strong
10—Very strong Results in table 1 show dry cloth performance results for the "rubbed" evaluations, for both unstored Fabric Softener samples ("Fresh") and those stored for four weeks at 37° C. ("Stored")—separate scores for Line and Tumble drying are given for the Fresh samples, and an average of those two scores for the Stored samples.

Accordingly, particular preference is given to a microcapsule as described above, said microcapsule having a percentage of fragrance leakage measured by the "fragrance leakage test" of less than 10% by weight.

TABLE 1

| Sample | Stirring speed of emulsion premix/ RPM | Dial M per dispersion/ wt % | Solid content theo./wt % | Solid content exp./% | Ø/μm | Line Dry Performance Initial | Tumble Dry Performance Initial | Overall Performance after Storage at 37° C. | % Leakage (after 2 weeks at 37° C.) |
|---|---|---|---|---|---|---|---|---|---|
| 1 | 250[a] | 20 | 40 | 41.9 | 29.9 | 7 | 7 | 7 | 3.1 |
| 2 | 250[a] | 20 | 40 | 39.9 | 26.6 | 7 | 7 | 6 | 2.2 |
| 3 | 250[a] | 25 | 40 | 40.4 | 37.4 | 8 | 7 | 8 | 1.4 |
| 4 | 250[b] | 20 | 40 | 38.0 | 25.3 | 6 | 5 | 6 | 6.4 |
| 5 | 250[b] | 25 | 40 | 39.0 | 28.4 | 6 | 5 | 9 | 7.3 |
| 6 | 200[b] | 25 | 40 | 40.04 | 46.4 | 5 | 5 | 6 | 8 |

TABLE 1-continued

| Sample | Stirring speed of emulsion premix/ RPM | Dial M per dispersion/ wt % | Solid content theo./wt % | Solid content exp./% | Ø/μm | Line Dry Performance Initial | Tumble Dry Performance Initial | Overall Performance after Storage at 37° C. | % Leakage (after 2 weeks at 37° C.) |
|---|---|---|---|---|---|---|---|---|---|
| 7 | 200[a] | 25 | 40 | 40.84 | 48.3 | 6 | 6 | 5 | 7 |
| 8 | 200[a] | 25 | 40 | 39.9 | 55.1 | 4 | 3 | 3 | 10.6 |
| 9 | 3500[c] | 31 | 40 | 41 | 3.4 | 5 | 5 | | 35 |
| 10 | 3500[C] | 20 | 40 | 38.9 | 2.9 | 2 | 3 | 3 | 44.4 |
| 11 | 100[a] | 25 | 40 | | | | coagulated | | |

[a]Anchor-type stirring blade,
[b]MIG ©-stirrer,
[c]High-speed dissolver stirrer (disc diameter 5 cm)

The invention claimed is:

1. A microcapsule comprising a core of hydrophobic material comprising at least one fragrance and a microcapsule shell obtainable by the suspension polymerization of the following monomers;
   (a) one or more $C_1$-$C_{24}$-alkyl ester of (meth)acrylic acid (monomer A),
   (b) one or more bi- or polyfunctional monomer (monomer B) and
   (c) optionally, one or more other ethylenically unsaturated monomer (monomer C),
      wherein an emulsion is prepared with a shear rate for the preparation of the emulsion in the range of from 150 to 500 rpm, and with a stirring time for the preparation of the emulsion in the range of from 15 min to 180 min, using an anchor-type stirring blade or a MIG-stirrer, wherein the microcapsule has a mean diameter in the range from 25 to 50 μm.

2. The microcapsule of claim 1, wherein the shear rate for the preparation of the emulsion is in the range of from 150 to 350 rpm.

3. The microcapsule of claim 1, wherein the stirring time for the preparation of the emulsion is in the range of from 20 min to 40 min.

4. The microcapsule of claim 1, wherein said microcapsule has a mean diameter in the range from 30 to 45 μm.

5. The microcapsule of claim 1, wherein said microcapsule consists essentially of the following monomers in copolymerized form:
   (a) from 20 to 60% by weight of said monomer A,
   (b) from 20 to 60% by weight of said monomer B, and
   (c) from 0 to 60% by weight of said monomer C.

6. The microcapsule of claim 1, wherein said microcapsule consists essentially of the following monomers in copolymerized form:
   (a) from 25 to 45% by weight of said monomer A,
   (b) from 25 to 45% by weight of said monomer B, and
   (c) from 30 to 50% by weight of said monomer C.

7. The microcapsule of claim 1, wherein said monomer A is methyl methacrylate.

8. The microcapsule of claim 1, wherein said monomer B is 1,4-butanediol diacrylate, pentaerythrityl triacrylate, ethylene glycol dimethacrylate, pentaerythrityl tetraacrylate, or mixtures thereof.

9. The microcapsule of claim 1, wherein said monomer C is methacrylic acid.

10. A fabric and home care composition containing the microcapsule of claim 1, said fabric and home care composition selected from the group consisting of solid and liquid laundry detergent compositions and liquid fabric softeners and conditioners.

11. A cosmetic formulation containing the microcapsule of claim 1.

12. The cosmetic formulation of claim 11, wherein the cosmetic formulation is a shampoo or a hair conditioning formulation.

13. A laundry or cosmetic formulation comprising the microcapsule of claim 1, wherein the laundry or cosmetic formulation has a percentage of fragrance leakage, measured by the "fragrance leakage test", of less than 10% by weight.

14. The microcapsule of claim 5, having a fragrance leakage of less than 10% by weight as measured by capillary gas chromatography.

15. The microcapsule of claim 5, wherein said monomer A is methyl methacrylate, and monomer B is selected from 1,4-butanediol diacrylate, pentaerythrityl triacrylate, ethylene glycol dimethacrylate, pentaerythrityl tetraacrylate, or mixtures thereof.

16. The microcapsule of claim 15, having a fragrance leakage of less than 10% by weight as measured by capillary as chromatography.

17. The microcapsule of claim 1, wherein said microcapsule has a mean diameter in the range from 25.3 to 46.4 μm, and a fragrance leakage in the range of 1.4% to 8% by weight as measured by capillary gas chromatography.

* * * * *